US009764123B2

(12) United States Patent
Sano et al.

(10) Patent No.: US 9,764,123 B2
(45) Date of Patent: Sep. 19, 2017

(54) NEEDLE-LESS CONNECTOR

(71) Applicant: NIPRO CORPORATION, Osaka-shi, Osaka (JP)

(72) Inventors: Yoshihiko Sano, Osaka (JP); Hiroshi Matsuo, Osaka (JP); Ken Suzuki, Osaka (JP)

(73) Assignee: NIPRO CORPORATION, Osaka (JP)

( * ) Notice: Subject to any disclaimer, the term of this patent is extended or adjusted under 35 U.S.C. 154(b) by 0 days.

(21) Appl. No.: 14/375,658

(22) PCT Filed: Feb. 12, 2013

(86) PCT No.: PCT/JP2013/000737
§ 371 (c)(1),
(2) Date: Jul. 30, 2014

(87) PCT Pub. No.: WO2013/121769
PCT Pub. Date: Aug. 22, 2013

(65) Prior Publication Data
US 2014/0371686 A1    Dec. 18, 2014

(30) Foreign Application Priority Data

Feb. 13, 2012 (JP) .................................. 2012-028449

(51) Int. Cl.
*A61M 39/02* (2006.01)
*A61M 5/168* (2006.01)
(Continued)

(52) U.S. Cl.
CPC ............ *A61M 39/02* (2013.01); *A61M 5/168* (2013.01); *A61M 39/10* (2013.01); *A61M 39/26* (2013.01);
(Continued)

(58) Field of Classification Search
CPC ...... A61M 39/00; A61M 39/02; A61M 39/10; A61M 5/168
See application file for complete search history.

(56) References Cited

U.S. PATENT DOCUMENTS

| 6,050,978 A | 4/2000 | Orr et al. |
|---|---|---|
| 6,171,287 B1 | 1/2001 | Lynn et al. |

(Continued)

FOREIGN PATENT DOCUMENTS

| CN | 101534881 A | 9/2009 |
|---|---|---|
| JP | A-2002-516160 | 6/2002 |

(Continued)

OTHER PUBLICATIONS

International Search Report issued in International Patent Application No. PCT/JP2013/000737 mailed Apr. 16, 2013.
(Continued)

*Primary Examiner* — Imani Hayman
(74) *Attorney, Agent, or Firm* — Oliff PLC

(57) ABSTRACT

A needle-less connector includes a housing having a drug solution flow path, and an elastic valve body. An end surface of the housing on a side of a tip end opening of the drug solution flow path constitutes a protruding support surface whose center section protrudes and slopes in a direction of a foot, and the elastic valve body is superposed onto the protruding support surface in a state of close contact therewith. Insertion of a male luer into a slit of the elastic valve body causes expanding deformation of the elastic valve body along the protruding support surface. A flexion section is formed on a sloped surface of the protruding support surface, and the sloped surface has different tilt angles on a foot section side and on a crest section side of the flexion section.

11 Claims, 8 Drawing Sheets

(51) Int. Cl.
  *A61M 39/10* (2006.01)
  *A61M 39/26* (2006.01)
  *A61M 39/00* (2006.01)

(52) U.S. Cl.
  CPC ............... *A61M 2039/0072* (2013.01); *A61M 2039/267* (2013.01)

(56) References Cited

U.S. PATENT DOCUMENTS

| | | |
|---|---|---|
| 7,806,890 B2 | 10/2010 | McKinnon et al. |
| 8,540,677 B2 | 9/2013 | McKinnon et al. |
| 2002/0002351 A1 | 1/2002 | Cote et al. |
| 2008/0132877 A1 | 6/2008 | McKinnon et al. |
| 2010/0030163 A1 | 2/2010 | Carrez et al. |
| 2011/0074148 A1 | 3/2011 | Imai |

FOREIGN PATENT DOCUMENTS

| | | |
|---|---|---|
| JP | A-2009-544449 | 12/2009 |
| JP | A-2010-508986 | 3/2010 |
| JP | A-2010-514528 | 5/2010 |
| WO | 9721463 A1 | 6/1997 |
| WO | 2008081027 A1 | 7/2008 |
| WO | WO 2009/133754 A1 | 11/2009 |

OTHER PUBLICATIONS

Aug. 19, 2014 Translation of International Preliminary Report on Patentability issued in International Application No. PCT/JP2013/000737.

Oct. 2, 2015 Search Report issued in European Application No. 13749341.7.

Sep. 28, 2016 Office Action issued in Japanese Application No. 2014-500101.

Dec. 31, 2015 Office Action issued in Chinese Patent Application No. 201380009202.6.

NEEDLE-LESS CONNECTOR

TECHNICAL FIELD

The present invention is related to a needle-less connector used in the medical field for a liquid passage such as an infusion route in which a male luer provided on a device such as a syringe can be connected to the liquid passage.

BACKGROUND ART

In the medical field, needle-less connectors are sometimes used in infusion or blood transfusion liquid passages in order to enable the connection and separation of syringes or transfusion bags. Such needle-less connectors have an elastic valve body provided at the tip end opening of a drug solution flow path formed in a housing as described in FIG. 1 of the specifications of U.S. Pat. No. 6,171,287 (Patent Document 1). The base end of the drug solution flow path can be connected to a catheter, where the connection between the catheter inserted into the blood vessel and base end of the drug solution flow path connects the drug solution flow path and the blood vessel.

The insertion from outside of the male luer into a slit which is formed in the elastic valve body so as to penetrate therethrough, opens the elastic valve body and connects the drug solution flow path and the male luer. In this state, medical liquid is made to flow into the needle-less connector from a syringe and the like connected to the male luer to administer the medical liquid to the patient. Once the administration of the medical liquid is completed, the male luer is extracted from the slit, which closes with the recovery of the elastic valve both to its original state. As a result, the tip end opening of the drug solution flow path is cut off by the elastic valve body, enabling the male luer to be separated from the drug solution flow path connected to the blood vessel and the like.

When extracting the male luer from the slit in a needle-less connector, blood may enter the catheter connected to the drug solution flow path from the blood vessel (back flow of blood), creating a risk of blood coagulation. This led to demand for a needle-less connector in which the back flow of blood upon extraction of the male luer from the slit could be prevented.

The needle-less connector as described in the above Patent Document 1 has a conventional structure in which the tip end opening of the drug solution flow path gradually widens towards the elastic valve body. However, in this structure, since the end surface of the drug solution flow path side at the elastic valve body is not supported, the central section of the elastic valve body undergoes elastic deformation inwards from the tip end opening of the drug solution flow path when inserting the male luer from outside. As a result, the extraction of the male luer causes an expansion in the volume of the drug solution flow path connected to the blood vessel which accompanies the recovery of the elastic valve body to its original state. This creates a suction force of blood to the drug solution flow path, increasing the risk of the back flow of blood.

Japanese Domestic Publication of International Patent Application No. JP-A-2009-544449 (Patent Document 2) proposes a structure in order to prevent such a back flow of blood which involves the embedding of a hard material along with the formation of an inside chamber in the partition or valve. In this structure, as described in Patent Document 2, the back flow of blood is prevented by an expansion of the volume of the inside chamber which accompanies the elastic deformation of the partition when inserting the tip end section of the male luer, which then causes a reduction in the volume of the inside chamber upon extraction of the tip end section.

However, even in the structure as described in Patent Document 2, although the inside chamber was extended with the insertion of the tip end section of the male luer into the partition or valve, the partition would deform so as to penetrate the inside chamber and a sufficient expansion of the inside chamber was difficult to achieve. Thus, it was difficult to demonstrate a sufficient effect of preventing the back flow of blood. In addition, manufacturing was made difficult due to the compound structure of the partition or valve with a hard material as well as its complex shape. There was also the problem that handling may be more difficult as a result of increased rigidity due to the restriction of the elastic deformation of the elastic body partition by the hard material as well as the difficulty of having sufficient durability to deal with the risk of cracking due to the concentration of deforming stress.

BACKGROUND ART DOCUMENTS

Patent Documents

Patent Document 1: U.S. Pat. No. 6,171,287
Patent Document 2: JP-A-2009-544449

SUMMARY OF THE INVENTION

Problem the Invention Attempts to Solve

With the foregoing in view, it is an object of the present invention to provide a novel needle-less connector configured so that the back flow of blood and the like can be prevented by a simple structure.

Means for Solving the Problem

In order to solve the above problems, as first mode of the present invention provides a needle-less connector including: a housing having a drug solution flow path; and an elastic valve body provided at a tip end opening of the drug solution flow path while having a slit formed penetrating therethrough such that insertion of a male luer into the slit opens the elastic valve body and connects the male luer to the drug solution flow path, the needle-less connector being characterized in that: an end surface of the housing on a side of the tip end opening of the drug solution flow path constitutes a protruding support surface whose center section protrudes and slopes in a direction of a foot, and the elastic valve body is superposed onto the protruding support surface in a state of close contact therewith; the insertion of the male luer into the slit of the elastic valve body causes expanding deformation of the elastic valve body along the protruding support surface; and a flexion section is formed on a sloped surface of the protruding support surface, and the sloped surface has different tilt angles on a foot section side and on a crest section side of the flexion section.

In the needle-less connector according to the present mode, by superposing the elastic valve body onto the protruding support surface so as to be in close contact therewith, the elastic valve body elastically deforms upon insertion of the male luer so as to be pushed to open in the slit expansion direction along the protruding support surface. As a result, the penetration of the elastic valve body into the drug solution flow path side is prevented upon insertion of the male luer, and the volume between the elastic valve body and the protruding support surface is increased by the amount of expansion of the slit. Thus, when the male luer is extracted, the volume reduction corresponding to the amount of closure of the expanded slit generates a positive pressure on the drug solution flow path, effectively preventing the back flow of blood and the like.

In the needle-less connector of the present mode, given that a flexion section is formed in the protruding support surface, a bending section is also formed on the elastic valve body which is closely superposed onto the protruding support surface at a position corresponding to the flexion section. Thus, when the elastic valve body deforms along the protruding support surface upon insertion of the male luer, a bending deformation readily occurs in the bending section in an outwardly-separating direction from the protruding support surface. This reduces the deformation rigidity of the elastic valve body, making the insertion of the male luer easier. In addition, a gap occurs more readily between the flexion section of the protruding support surface and the bending section of the elastic valve body. This gap further increases the volume within the elastic valve body upon insertion of the male luer, generating an even larger positive pressure on the drug solution flow path when extracting the male luer. This can result in a further improvement in the prevention of the back flow of blood and the like. In the cross-section of the protruding support surface, the sloped surface constitutes curved or straight lines. The flexion section of the present invention corresponds to the inflection point or intersection of the curved lines or straight lines on the sloped surface.

A second mode of the present invention provides the needle-less connector according to the first mode, wherein a deformation allowance space is provided on an outer peripheral side of the elastic valve body.

In this mode, a space is provided on the outer peripheral side of the elastic valve body so that, when the elastic valve body undergoes elastic deformation along the protruding support surface upon insertion of the male luer, the elastic valve body is able to undergo such deformation. This space on the outer peripheral side allows an easier deformation of the elastic valve body and may also lead to improved operability of male luer insertion. The structure of the elastic valve body is also simplified compared to cases in which the elastic valve body deformation space is provided inside the elastic valve body.

A third mode of the present invention provides the needle-less connector according to the first or second mode, wherein the elastic valve body integrally includes a valve body part in which the slit is formed penetrating therethrough and a pair of flange parts arranged at both ends of the slit of the valve body part in a direction of penetration and each extending to the outer peripheral side, and an outer peripheral edge part of each flange part is fixed to and supported by the housing, and elastic deformation of the elastic valve body is allowed between opposing faces of the flange parts.

In this mode, the elastic valve body is provided with as pair of flange parts. The elastic valve body is fixed to and supported by the housing at the outer peripheral edge part of the flange parts to ensure the seal efficiency of the inner fluid and elastic valve body slit, where the provision of the deformation allowance space enables easier elastic deformation at the valve body part when inserting the male luer. This results in a further increase in the volume within the elastic valve body upon insertion of the male luer and may lead to a further improvement in the prevention of the back flow of blood and the like upon extraction of the male luer.

A fourth mode of the present invention provides the needle-less connector according to any of the first through third modes, wherein a space communication passage is formed to enable communication between an outer space and an area provided on the outer peripheral side of the elastic valve body and allowing the elastic deformation of the elastic valve body.

In this mode, deformation resistance due to the deformation allowance space air spring is avoided upon diameter enlarging deformation of the elastic valve body due to the insertion of the male luer. This results in easier insertion of the male luer into the elastic valve body, and a gap is more readily formed between the elastic valve body and the protruding support surface, leading to a further improvement in the prevention of the back flow of blood and the like upon extraction of the male luer.

A fifth mode of the present invention provides the needle-less connector according to any of the first through fourth modes, wherein an elastic secondary valve body is provided so as to be superposed onto an outer end surface of the elastic valve body, and a slit provided on the secondary valve body for insertion of the male luer extends in a direction to intersect the slit of the elastic valve body and be superposed thereto.

In this mode, in both the elastic valve body and the secondary valve body, the slit is opened or closed based on the elastic deformation which accompanies the insertion or extraction of the male luer, enabling the communication/cut off of the drug solution flow path. Since these two valve bodies are superposed with the respective slits in an intersected state, seal efficiency of the outer space of the drug solution flow path can be favorably maintained at the time of inserting and extracting the male luer.

A sixth mode of the present invention provides the needle-less connector according to any of the first through fifth modes, wherein at least a tip end section of the protruding support surface extends in a mountain-like shape by means of a ridge-shaped apex, the flexion section is formed on the sloped surface on each side of the ridge-shaped apex, and the slit of the elastic valve body is superposed so as to extend along the ridge-shaped apex of the protruding support surface.

In this mode, the opposite sections of the slit of the elastic valve body are guided along the sloped surfaces on opposite sides of the protruding support surface when the male luer is inserted into the slit of the elastic valve body. This results in elastic deformation of the slit in the direction of expansion. The guiding action by the protruding support surface and the slit expansion direction combine to result in a more efficient and stable elastic deformation of the elastic valve body. Due to this, the insertion of a male luer forms a large gap between the elastic valve body and the protruding support surface, enabling a more efficient means of preventing the back flow of blood and the like upon extraction of the male luer.

A seventh mode of the present invention provides the needle-less connector according to any of the first through sixth modes, wherein the sloped surface on the crest section side of the flexion section in the protruding support surface constitutes a recessed curved surface.

In this mode, the guiding action at the time of deformation of the elastic valve body, especially due to the recessed curved surface of the protruding support surface, enables easier elastic deformation of the elastic valve body upon insertion of the male luer as well as easier operability upon insertion of the male luer. The elastic valve body separates significantly from the flexion section of the protruding support surface to allow for easier deformation. This improves the prevention of the back flow of blood and the like upon extraction of the male luer.

An eighth mode of the present invention provides the needle-less connector according to any of the first through seventh modes, wherein the foot section side of the flexion section in the protruding support surface has a tapered surface.

In this mode, the guiding action of the tapered foot section side of the protruding support surface enables easier elastic deformation of the elastic valve body in the direction of expansion over the entire circumference of the elastic valve body upon insertion of the male luer. This lowers the insertion resistance of the male luer into the elastic valve body and improves workability.

A ninth mode of the present invention provides the needle-less connector according to any of the first through eighth modes, wherein the tip end opening of the drug solution flow path has a nozzle shape whose cross-sectional area is reduced.

In this mode, the small opening area of the tip end opening of the drug solution flow path which opens onto the protruding support surface prevents flaws such as the elastic valve body entering into the tip end opening.

Effect of the Invention

In the needle-less connector having a structure in conformance with the present invention, the deformation of the elastic valve body upon insertion of the male luer occurs in the direction away from the protruding support surface based on the guiding action of the protruding support surface inflection points. This gives rise to a gap between the elastic valve body and the protruding support surface upon insertion of the male luer, and the back flow of blood and the like is prevented by a positive pressure generated by the disappearance of such gap upon extraction of the male luer.

EMBODIMENTS FOR CARRYING OUT THE INVENTION

Figure 1:
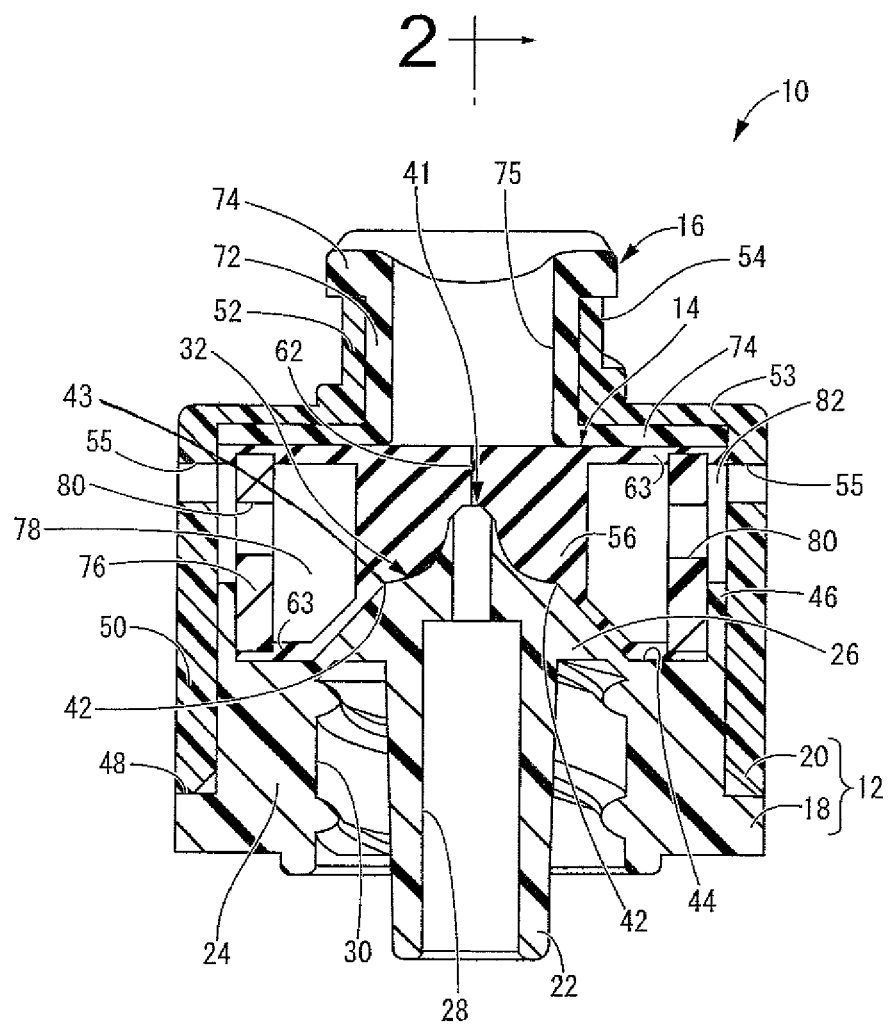
FIG. 1 is a longitudinal cross section view of a needle-less connector as a first embodiment of the present invention.
Figure 2:
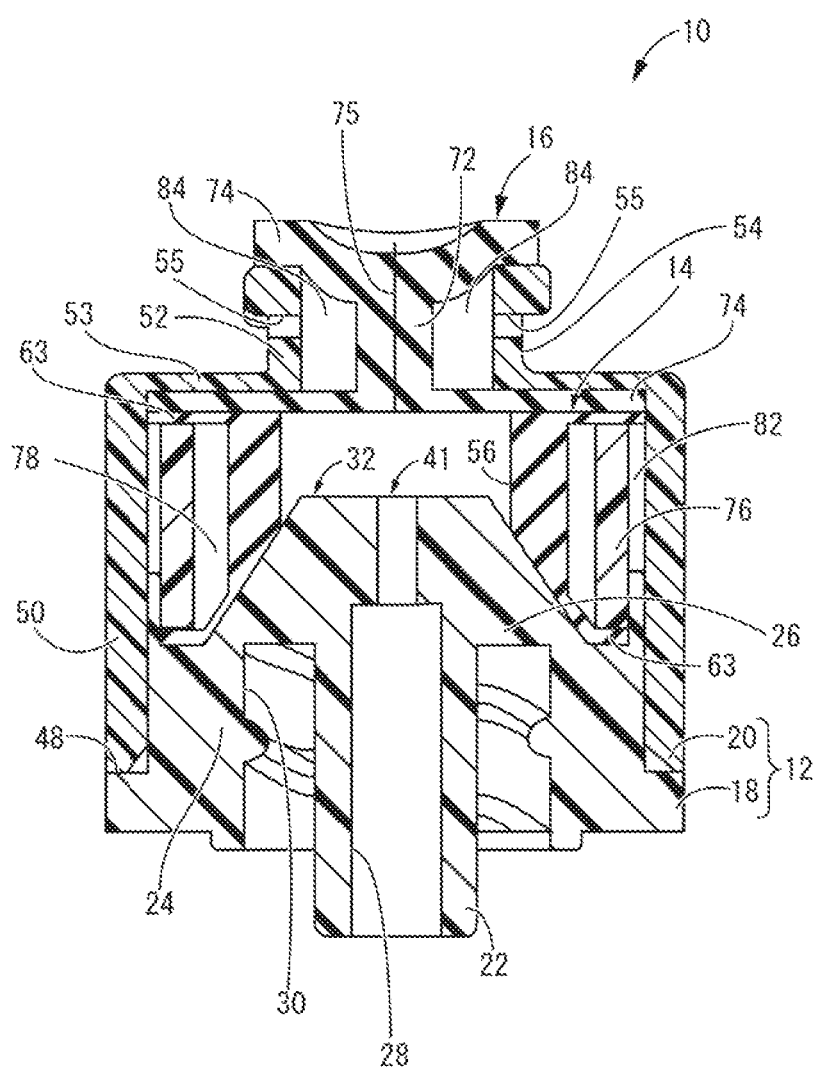
FIG. 2 is a cross section view taken along line 2-2 of FIG. 1.

The embodiments of the present invention are described below with reference to the drawings in order to further clarify the present invention. FIGS. 1 and 2 show a needle-less connector 10 as a first embodiment of the present invention. This needle-less connector 10 has a structure in which a housing 12 is equipped with a lower valve 14 as an elastic valve body and an upper valve 16 as a secondary valve body. In the description below, the vertical direction refers to the vertical direction in FIGS. 1 and 2.

The housing 12 constitutes a block construction, which includes a base housing 18 of the base end side or the upper part of FIG. 1 and a cover housing 20 of the tip end side or the upper end of FIG. 1.

The base housing 18 has a peripheral wall part 24 provided away from the outer circumferential side of a cylindrical part 22 which extends over a center axis, where the upper end sections of the cylindrical part 22 and the peripheral wall part 24 are integrally connected by a top wall part 26. The cylindrical part 22 protrudes downwards from the peripheral wall part 24 and a drug solution flow path 28 is formed within the cylindrical part 22. A locking groove 30 is formed on the inner circumferential surface of the peripheral wall part 24.

An intravascular indwelling catheter, which is not illustrated, can be connected to the base end opening part of the cylindrical part 22 of the base housing 18. The structure provided in this embodiment is a lock-type luer structure based on the cylindrical part 22 and the peripheral wall part 24 which enables the secure connection of the intravascular indwelling catheter.

Figure 3:
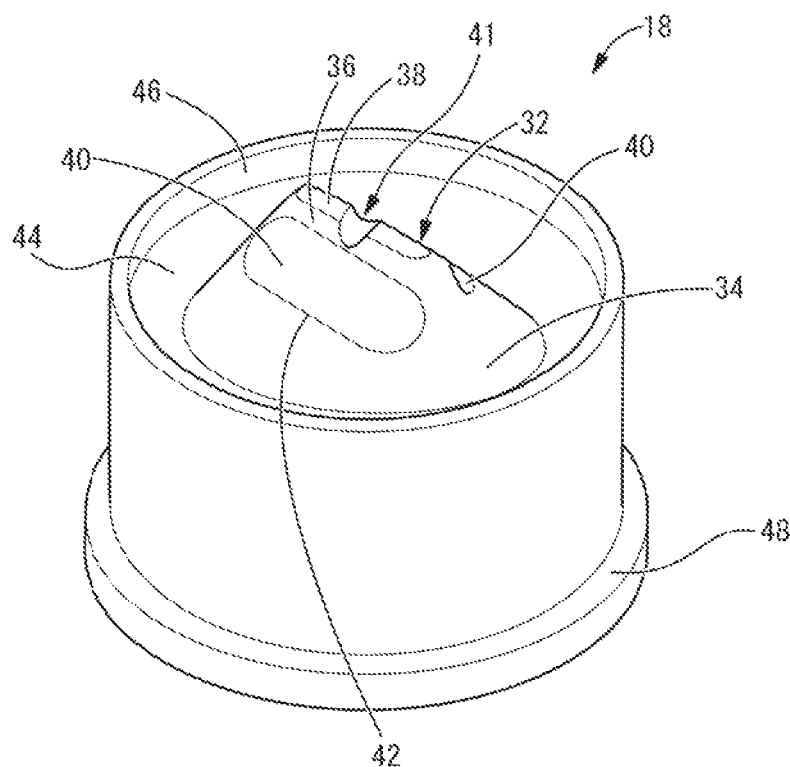
FIG. 3 is a perspective view of a base housing constituting the needle-less connector shown in FIG. 1.
Figure 4:
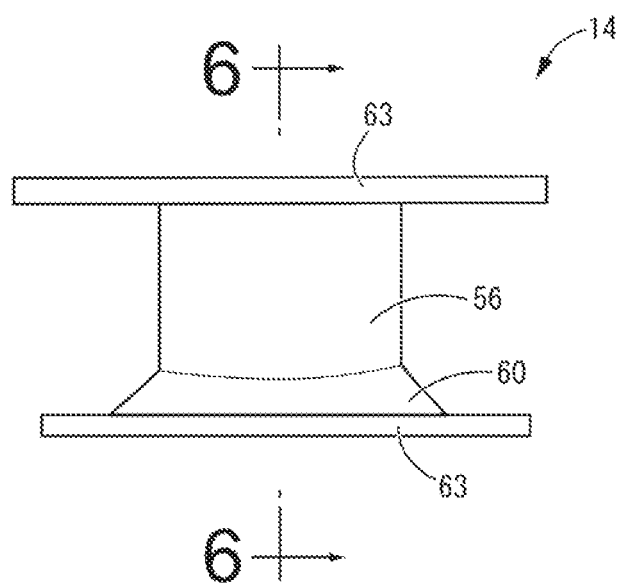
FIG. 4 is a front view of an elastic valve body constituting the needle-less connector shown in FIG. 1.
Figure 5:
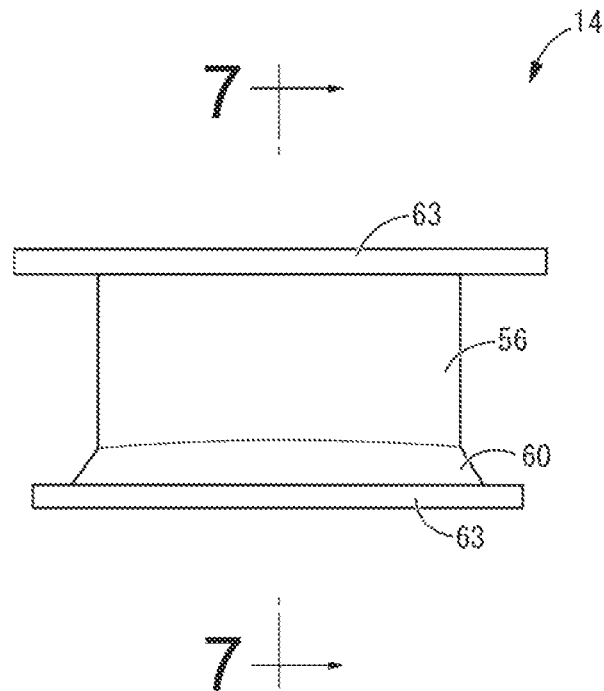
FIG. 5 is a right side view of the elastic valve body shown in FIG. 4.
Figure 6:
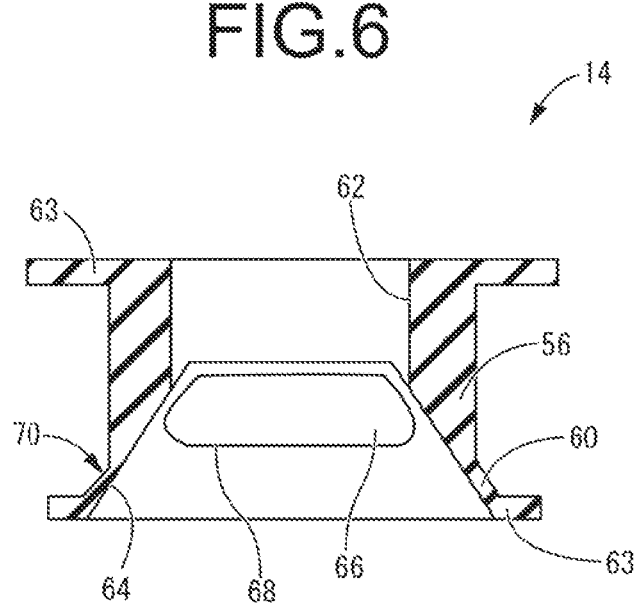
FIG. 6 is a cross section view taken along line 6-6 of FIG. 4.
Figure 7:
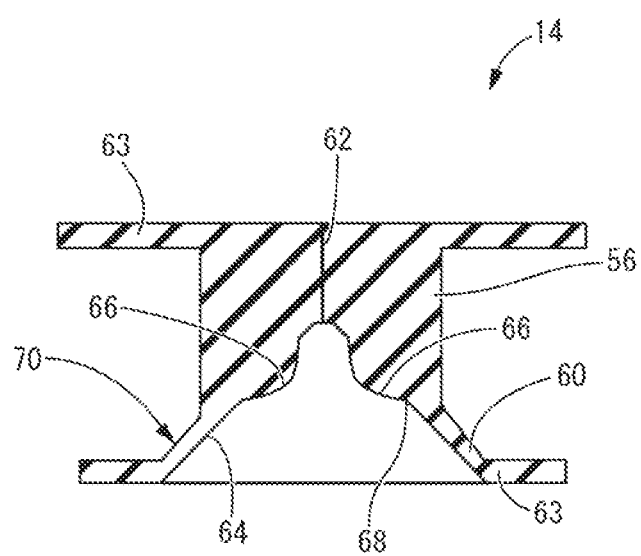
FIG. 7 is a cress section view taken along line 7-7 of FIG. 5.

Formed on the upper end surface of the base housing 18, in which the cylindrical part 22 and the peripheral wall part 24 is connected by the top wall part 26, is a protruding support surface 32 which protrudes upwards at the center section in a mountain-like shape and which slopes in the direction of the foot. This protruding support surface 32, as also shown in FIG. 3, has a foot section side 34 and a crest section side 36. The surface of the foot section side 34 tapers upwards, decreasing in diameter. On the crest section side 36, recessed curved surfaces 40 and 40 are bored into the sloped surfaces on opposite sides of an apex 38, where the apex 38 has a mountain-like shape which extends in a ridge shape.

The drug solution flow path 28 formed in the cylindrical part 22 has in its upper part a nozzle-shaped tip end opening 41 with a reduced cross-sectional area. This nozzle-shaped tip end opening 41 opens onto the center of the apex 38 which extends in a ridge shape along the protruding support surface 32.

A flexion section 42 is formed on the border of the foot section side 34 and the crest section side 36 in the middle section of the sloped surface in the direction of height on each side of the apex 38 of the protruding support surface 32. This flexion section 42 extends on each side of the apex 38 along the lower end edge of the recessed curved surface 40 in the circumferential direction of the protruding support surface 32. A bending section 43 is also formed on the elastic valve body 14 which is closely superposed onto the protruding support surface 32 at a position corresponding to the flexion section 42, as shown in FIG. 1.

As also evident in FIG. 1, the tilt angle of the foot section side 34 and the tilt angle of the crest section side 36 which are positioned to opposite sides of the flexion section 42 are different. In this embodiment, since a recessed curved surface 40 is formed on the crest section side 36, the flexion section 42 has a cross-sectional profile which is curved outwardly in a convex manner.

In this embodiment, the tilt angle of the crest section side 36 near the flexion section 42 is smaller than the tilt angle of the foot section side 34 and larger than the tilt angle of the foot section side 34 near the apex 38. As shown by the cross-sectional profile of FIG. 1, this results in the tip end side on the crest section side 36 having a sharp, taper-shaped slope and the area near the flexion section 42 having a smooth, gentle slope.

A ring-shaped flat surface 44 which extends in a circumferential direction on the outer peripheral side of the protruding support surface 32 at a specified width is formed on the upper end surface of the base housing 18. An upward protruding cylindrical outer peripheral collar 46 is integrally formed at the outer peripheral edge part of the flat surface 44. A step 48 is formed at the outer peripheral surface of the base housing 18 in order to fix the positioning of the cover housing 20.

The cover housing 20 which, together with the base housing 18, constitutes such a housing 12, has an overall stepped cylindrical shape. In other words, the cover housing 20 includes a cover body 50 having a cylindrical-shaped large diameter and a connection port part 52 having a cylindrical-shaped small diameter which are integrally connected by an annular disk-shaped top wall part 53.

The cover body 50, which opens in a downward direction, is assembled from the upper part of the base housing 18 and the opening part of the cover body 50 is fitted to the outer peripheral surface of the base housing 18. The opening section of the cover body 50 is fixed to the base housing 18 and positioned in an axial direction by means of the step 48 of the base housing 18 by a fixing means such as press fitting, welding or adhesion.

Assembling the cover housing 20 to the base housing 18 in this manner forms an inner area surrounded by the cover housing 20 at the upper part of the base housing 18. This inner are opens upward via the connection port part 52 of the cover housing 20. A locking groove 54 is formed at the outer peripheral surface of the connection port part 52. An air vent hole 55 run through the respective circumferential walls of the cover body 50 and the connection port part 52 to connect the inside to the outside.

As mentioned above, a lower valve 14 and an upper valve 16 are built into the inner area formed within the housing 12.

The lower valve 14, as shown in FIGS. 4-7, has a block-shaped valve body part 56 having an oval-shaped outer peripheral surface, the lower side section of which is a large diameter part 60 having an outer peripheral surface shape which expands in a tapered form. A slit 62 is formed to penetrate the center section of the valve body part 56 in a vertical direction which expands in a longitudinal direction of the oval-shaped outer peripheral surface. A pair of flange parts 63 and 63 is integrally formed on both ends of the slit 62 in the direction of penetration at the outer peripheral surface of both upper and lower ends of the valve body part 56.

The upper end surface of the lower valve 14 is a flat surface and a recess 64 is formed which opens onto the center section of the lower end surface. This recess 64 has an inside surface shape corresponding to the outer surface shape of the protruding support surface 32 of the above base housing 18.

The inner circumferential surface of the opening side of the recess 64 has a tapered shape corresponding to the foot section side 34 of the protruding support surface 32. The inner circumferential surface of the upper bottom side of the recess 64 has a shape corresponding to the crest section side 36 of the protruding support surface 32. Convex curved surfaces 66 and 66 corresponding to the recessed curved surfaces 40 and 40 of the protruding support surface 32 are formed on opposite sides of the valley line extending in a straight line.

The slit 62 at the lower valve 14 is formed along the valley line of the recess 64. Flexion sections 68 and 68 are formed to extend along the lower end edge of the convex curved surfaces 66 and 66 at a position corresponding to the flexion sections 42 and 42 of the protruding support surface 32 at the middle section of the inner circumferential surface of the recess 64 in the direction of depth. In this embodiment, the flexion sections 68 and 68 are positioned higher up than the taper-shaped foot section in the valve body part 56. An opening section of the recess 64 is formed inside the taper-shaped foot section in the valve body part 56, where the foot section is a thin tapered cylindrical part 70.

The upper valve 16, as shown in FIGS. 1 and 2, has a block-shaped valve body part 72 having an oval-shaped outer peripheral surface. A pair of flange parts 74 and 74 is integrally formed on the outer peripheral surface of both top and bottom ends of the valve body part 72. At the center section of the valve body part 72, a slit 75 extending longitudinally to the oval-shaped outer peripheral surface is formed to penetrate therethrough in a vertical direction.

The lower valve 14 and the upper valve 16 are assembled within the housing 12 in such a way that the upper valve 16 is superposed onto the upper side end surface of the lower valve 14. Here, the inner surface of the recess 64 of the lower valve 14 is substantially superposed over the entire surface of the protruding support surface 32 of the base housing 18 in a state of nearly close contact therewith. The slit 62 of the lower valve 14 is superposed so as to extend along the ridge-shaped apex 38 of the protruding support surface 32. The lower side flange part 63 of the lower valve 14 is superposed in a state of nearly close contact onto the flat surface 44 of the base housing 18 on the outer peripheral side of the protruding support surface 32.

The lower side flange part 74 of the upper valve 16 is superposed onto the upper side flange part 63 of the lower valve 14. Both flange parts 63 and 74, having almost the same outer diameters, are superposed onto the lower surface of the top wall part 53 of the cover housing 20.

A cylinder-shaped holding sleeve 76 is inserted into the housing 12 and is arranged in the valve body part 56 of the lower valve 14 in a state of extrapolation. This holding sleeve 76 is fitted to and positioned in the lower end section of the outer peripheral collar 46 of the base housing 18, and is then mounted between the upper and lower flange parts 63 and 63 in the lower valve 14. As a result, the outer peripheral section of the flange part 63 of the lower side of the lower valve 14 is pushed against the flat surface 44 of the base housing 18 by the axial lower end surface of the holding sleeve 76 to be fixed to seal. In addition, the respective outer peripheral sections of the superposed flange part 63 of the upper side of the lower valve 14 and flange part 74 of the lower side of the upper valve 16 are pushed against the top wall part 53 of the cover housing 20 by the axial upper end surface of the holding sleeve 76 to be fixed to seal.

A deformation allowance space 78, which allows elastic deformation to the outer peripheral side of the lower valve 14, is formed on the outer peripheral side of the valve body part 56. In this embodiment in particular, the holding sleeve 76 is outwardly separated from the outer peripheral surface of the valve body part 56 of the lower valve 14, where the deformation allowance space 78 is formed between the valve body part 56 and the holding sleeve 76, or in other words, between the opposing faces of the upper and lower pair of flange parts 63 and 63 of the lower valve 14. A through hole 80 is formed in a radial direction to the holding sleeve 76 and a gap 82 is formed between the holding sleeve 76 and the cover body 50 of the cover housing 20. This forms a space communication passage which connects the deformation allowance space 78 to the outside space by means of the through hole 80, gap 82 and air vent hole 55.

In the upper valve 16, the valve body part 72 is arranged within the connection port part 53 of the cover housing 20. The flange part 74 of the upper side of the upper valve 16 is superposed onto the upper side opening end surface of the connection port part 52. A deformation allowance space 84, which allows elastic deformation of the valve body part 72 to the outer peripheral side, is formed between the valve body part 72 and the connection port part 52.

The lower valve 14 is aligned in a circumferential direction to the base housing 18 so that the longitudinal direction of the valve body part 56 extends in the direction of the ridgeline of the mountain-shaped apex 38 of the protruding support surface 32. Thus, the slit 62, which acts as the valve hole of the lower valve 14, extends along the ridgeline of the apex 38 of the protruding support surface 32 of the base housing 18. The slit 62 is in a state of close contact prior to the insertion of a male luer 92 mentioned below and is not open. On the lower side of the lower valve 14, the tip end opening 41 of the drug solution flow path 28 of the cylindrical part 22 opens onto the center of the apex 38 which extends in a ridge-shape along the protruding support surface 32.

The upper valve 16 is positioned in the circumferential direction and installed so that a slit 75, which acts as a valve opening, extends in a nearly orthogonal direction to the slit 62 of the lower valve 14. This ensures that the tip end opening 41 of the drug solution flow path 28 of the base housing 18 is positioned on the center axis which extends in a vertical direction via the intersection of the slit 62 of the lower valve 14 and the slit 75 of the upper valve 16.

Figure 8:
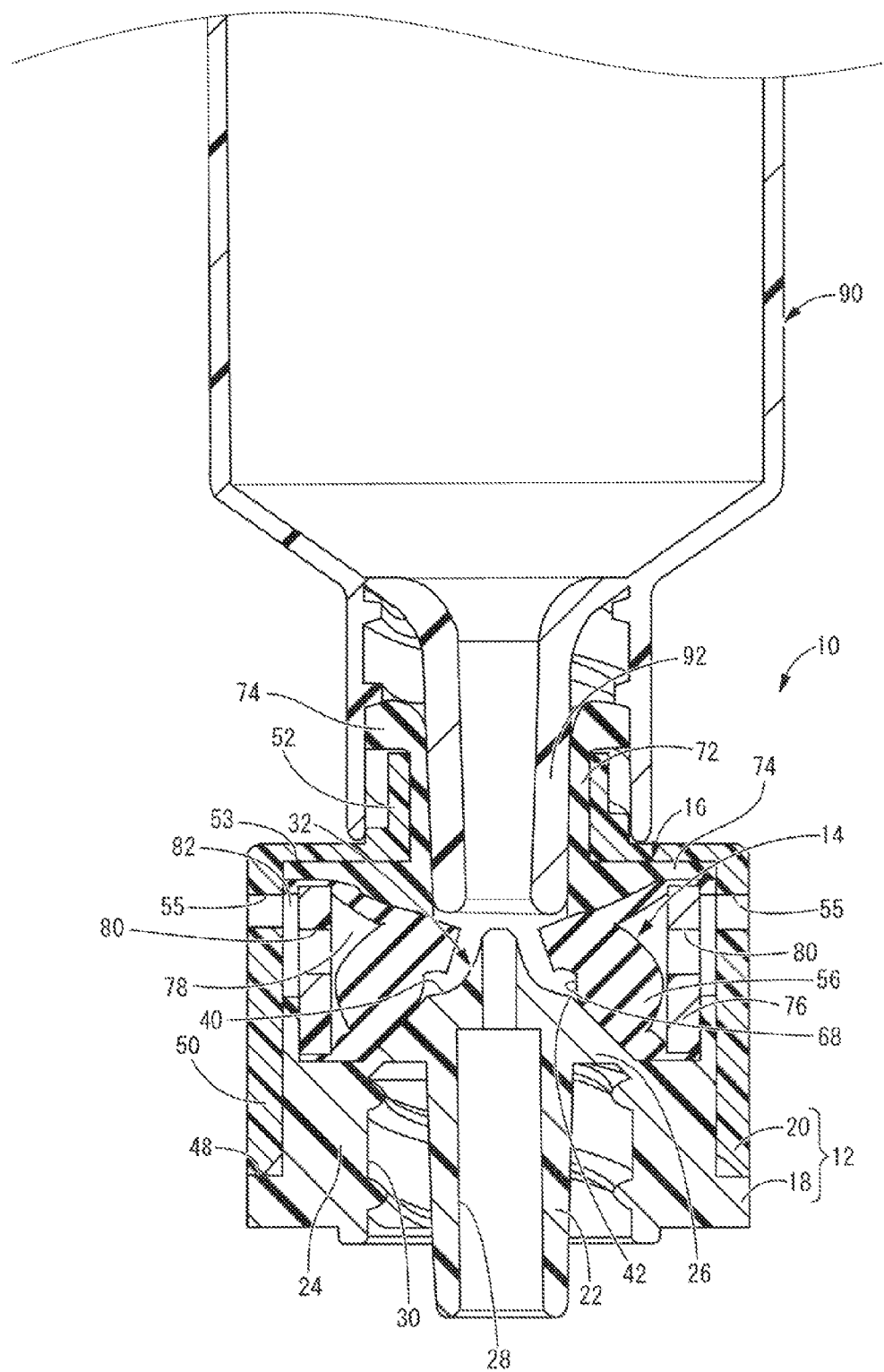
FIG. 8 is a view suitable for explaining a state of insertion of a male luer in the needle-less connector shown in FIG. 1.

In the needle-less connector 10 having the structure as mentioned above, an intravascular indwelling catheter and the like can be connected to the base end opening of the drug solution flow path 28 for use. As shown in FIG. 8, by inserting the male luer 92 such as a syringe 90 from the connection port part 52 of the housing 12, the respective slits 62 and 75 of the lower valve 14 and the upper valve 16 are expanded to connect the male luer 92 to the drug solution flow path 28.

The male luer 92 of the syringe 90 as shown in FIG. 8 has a male luer locking structure which maintains a secure connection with the connection port part 52 of the housing 12. In addition to a luer locking structure which is fixed using a screw, this male luer 92 may also have a luer slip structure which is fixed by insertion.

In the needle-less connector 10 of the present embodiment, the insertion force of the male luer 92 upon insertion of the same is transferred through to the lower valve 14, causing the center section of the valve body part 56 of the lower valve 14 to be pushed downwards. This downward push is accompanied by a deformation of the lower surface of the valve body part 56, which is pushed to expand to opposite sides of the slit 62 along the protruding support surface 32 which is in a close contact therewith.

Here, the flexion section 42 is formed in the direction of height in the middle section of the protruding support surface 32 which guides the valve body part 56 in the direction of deformation and a flexion section 68 corresponding to the flexion section 42 is also formed on the valve body part 56. In this embodiment, since the flexion section 42 in the protruding support surface 32 is outwardly convexed, the flexion section 68 at the valve body part 56 has a concave shape. As a result, when the valve body part 56 undergoes elastic deformation, the guiding action is more readily in an outward direction away from the flexion section 42 of the protruding support surface 32, and the valve body part 56 itself is more easily deformed so as to fold near the flexion section 68.

When the male luer 92 is inserted, the slit 62 of the lower valve 14 expands relatively easily, facilitating the deformation of the inner surface of the recess 64 of the lower valve 14 in an outward direction away from the protruding support surface 32. This enables passage communication operation due to the insertion of the male luer 92 to be carried out with ease. At the same time, the volume of the passage formed within the slit 62 of the lower valve 14 is actively increased. Thus, when the male luer 92 is extracted, the volume reduction corresponding to the amount of closure of the expanded slit 62 generates a positive pressure on the drug solution flow path 28, preventing the back flow of blood and the like.

In the needle-less connector 10 of this embodiment in particular, the recessed curved surface 40 is formed on the apex 38 side of the flexion section 42 in the protruding support surface 32. This enables the expanding deformation or the separating deformation from the protruding support surface 32 of the slit 62 of the lower valve 14 as mentioned above to be achieved more effectively upon insertion of the male luer 92. In addition, the crest section side 36 of the protruding support surface 32 has a mountain shape with a ridgeline extending in the same direction as the slit 62 of the lower valve 14. This enables the expansion and deformation or the separation and deformation from the protruding support surface 32 of the slit 62 of the lower valve 14 to be achieved even more effectively. This results in an even more favorable prevention of the back flow of blood and the like upon extraction of the male luer 92.

In this embodiment, the deformation allowance space 78 formed at the outer periphery of the lower valve 14 is connected to the outside space. As mentioned above, this results in an even more favorable elastic deformation of the lower valve 14 and effects based thereon. Since a space communication passage is not necessary in the present invention, the deformation allowance space 78 may also have a sealing structure.

Figure 9:
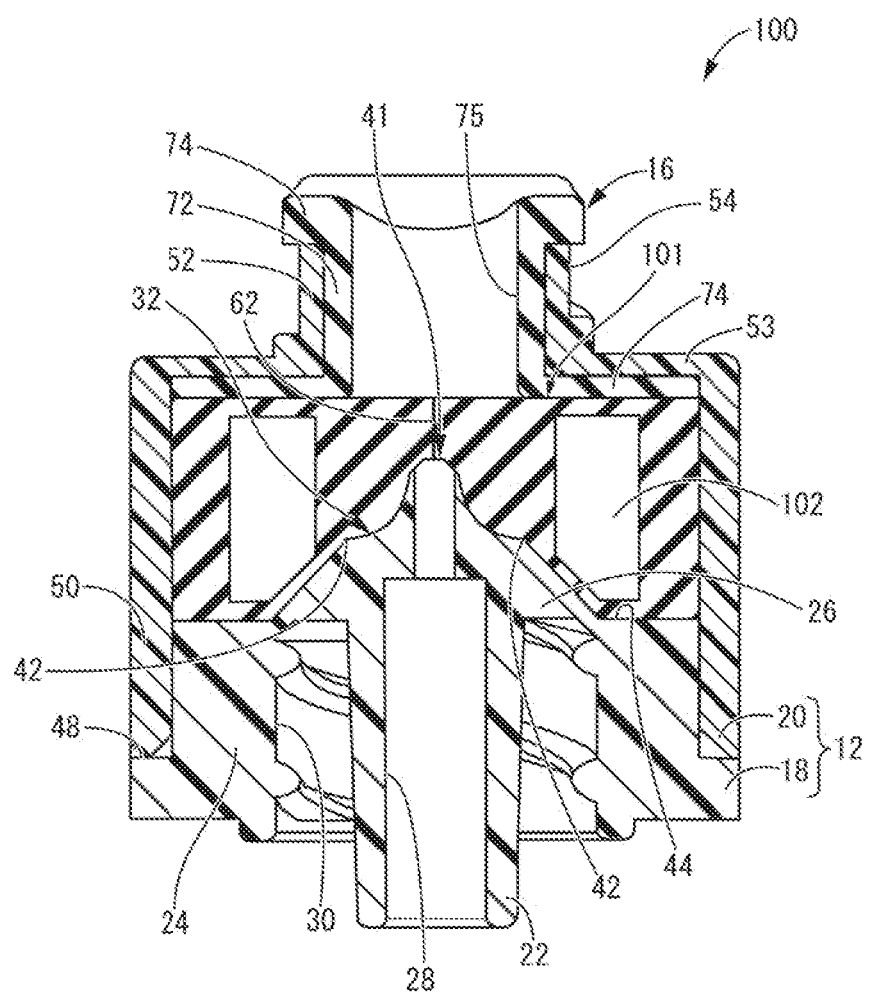
FIG. 9 is a longitudinal cross section view of a needle-less connector as a second embodiment of the present invention.

Next, a needle-less connector 100 according to a second embodiment of the present invention is shown in FIG. 9. Since the same symbols are used in FIG. 9 as in FIG. 1 concerning parts which are the same as those in the above first embodiment, the description thereof shall be abbreviated. In the above first embodiment, the deformation allowance space 78 is provided on the outer peripheral side of the valve body part 56, particularly between the valve body part 56 and the holding sleeve 76. In this embodiment, however, a sealed deformation allowance space 102 which allows elastic deformation of a lower valve 101 is provided in the inner part of the lower valve 101 or the elastic valve body. In this embodiment, the outer peripheral collar 46 of the base housing 18 or the holding sleeve 76 is not provided.

In the above first embodiment, the deformation allowance space 78 enables the elastic deformation of the lower valve 14 which accompanies the insertion of the male luer 92. At the time of elastic deformation, the compressed air is exhausted to the outside via the through hole 80, gap 82 and air vent hole 55. Deformation resistance due to the air spring within the deformation allowance space 78 is sufficiently small. This embodiment is the same in that the deformation allowance space 102 enables the elastic deformation of the lower valve 101 which accompanies the insertion of the male luer 92. Here, however, the deformation allowance space 102 has a sealed structure which creates as sufficient air spring effect due to the compressed air. When the lower valve 101 recovers its original state upon extraction of the male luer 92, an air spring action is obtained along with an elastic recovery force of the lower valve 101. As a result, the lower valve 101 is deformable so that the slit 62 of the lower valve 101 immediately assumes a closed state upon extraction of the male luer 92 even if a relatively soft material, a material having a large permanent compression set or a material which is difficult to recover its original state is used as the material of the lower valve 101. Pressure tightness (strength) is also increased.

Furthermore, it is not necessary for the deformation allowance space 102 to be continuous in a circumferential direction, where a plurality of independent or mutually-connected deformation allowance spaces may also be provided in a circumferential direction. In addition, it is not necessary for the deformation allowance space 102 in this embodiment to have a sealed structure, where it may be connected to and open into the outside space. In this case, the holding sleeve 76 or the outer peripheral collar 46 may be used as in the first embodiment. The shape of the deformation allowance space 102 in FIG. 9 has the same shape as the deformation allowance space 78 in FIG. 1. However, this is not limited to the above, where, in addition to singular polygonal or circular (including elliptical) shapes, the cross-section may be composed of a plurality of polygonal or circular shapes or a combination of the above.

Figure 10:
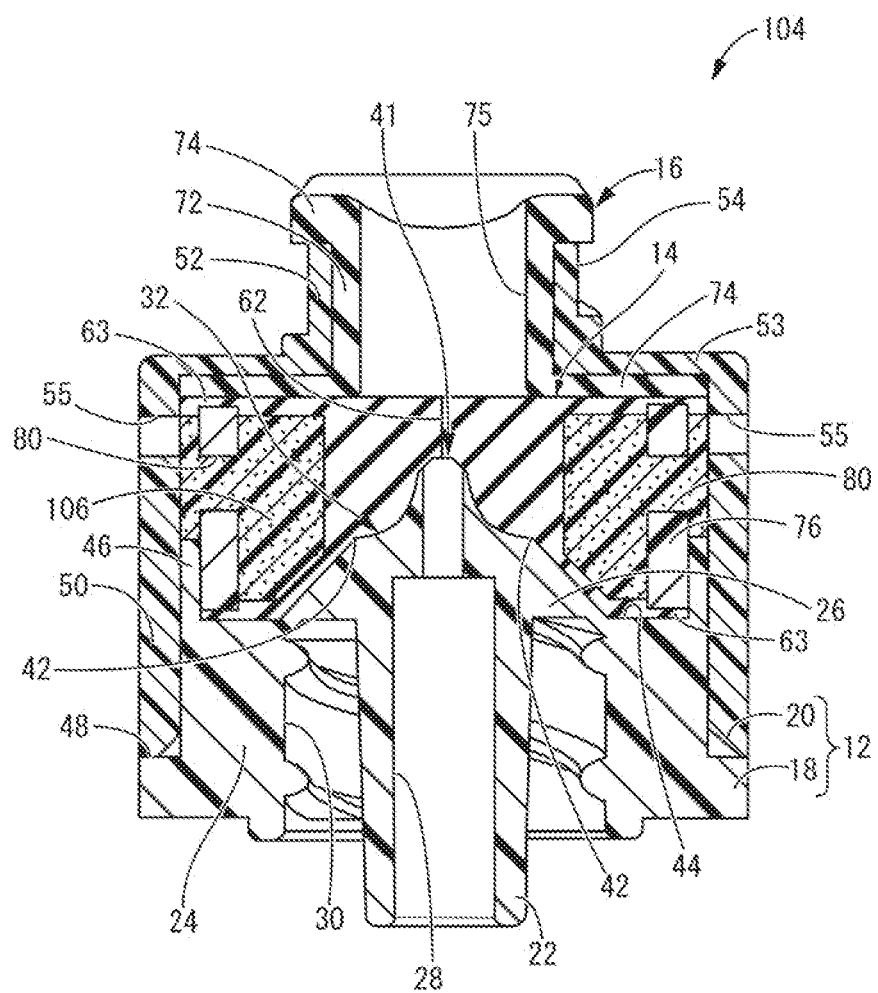
FIG. 10 is a longitudinal cross section view of a needle-less connector as a third embodiment of the present invention.

Next, a needless-connector 104 according to a third embodiment of the present invention is shown in FIG. 10. Since the same symbols are used in FIG. 10 as in FIG. 1 concerning parts which are the same as those in the above first embodiment, the description thereof shall be abbreviated. In the above first embodiment, a space having a specified volume (deformation allowance space 78) is provided to enable elastic deformation of the lower valve 14 upon insertion of the male luer 92. In this embodiment however, the deformation allowance space 78 (and through hole 80, gap 82) of the above first embodiment is filled with a synthetic foam 106 having spongiform open cells such as polyurethane. As in the first embodiment, the holding sleeve 76 is used in the third embodiment. The holding sleeve 76 is positioned and fixed by flange parts 63 and 63 of the lower valve 14. The synthetic foam 106 penetrates the through hole 80 of the holding sleeve 76. This positions and fixes the synthetic foam 106.

In the above first and second embodiments, elastic deformation of the lower valve 14 which accompanies the insertion of a male luer 92 is enabled by providing a space with a specified volume (deformation allowance spaces 78 and 102). In the third embodiment, a space is not provided due to the fact that the deformation allowance spaces 78 and 102 are filled with the synthetic foam 106. However, the synthetic foam 106 provides a substantial space inside comprised of open cells which are soft, highly elastic and flexible. This allows elastic deformation of the lower valve 14 due to compressive deformation upon insertion of the male luer 92, and the synthetic foam 106 changes shape to match the shape of the deformed lower valve 14. When the male luer 92 is extracted, the synthetic foam 106 changes shape to match the recovered shape of the lower valve 14 following recovery to its original state by means of recovering deformation, resulting in the sufficient prevention of the back flow of blood and the like. In this manner, instead of providing a space with a specified volume on the outer peripheral side or inside of the lower valve 14, a compressible and elastic member such as the synthetic foam 106 may be used to provide a substantial space. Furthermore, in the third embodiment, a space communication passage is constituted including the air vent hole 55, which connects the area provided on the outer peripheral side of the elastic valve body 14 and allowing the elastic deformation of the elastic valve body 14 to the outside space.

The embodiments of the present invention have been described above. However, the present invention is not limited to the description as provided in such embodiments and can be implemented in various additional forms including changes, modifications and improvements in accordance with the knowledge of the person skilled in the art.

For example, in this embodiment as different form of upper valve 16 is superposed onto the lower valve 14 and the respective slits 62 and 75 are positioned orthogonally to each other in a circumferential direction. Thus, when the male luer 92 is completely extracted from the slit 75 of the upper valve 16, the slit 62 of the lower valve 14 is closed. This enables an even more efficient prevention of any leakage of transfusion or blood and the like upon inserting or extracting the male luer 92. The orthogonal arrangement of the slits 75 and 62 of the upper valve 16 and the lower valve 14 are not necessary in the present invention, where only the lower valve 14 can be used without the upper valve 16. The upper valve 16 and the lower valve 14 may also be integrally formed. In this case, it is not necessary for the shape of the upper valve 16 and the lower valve 14 of FIG. 1 to match, where a flange part 63 may be formed only on the lower part of a valve. In such a valve shape which does not provide a flange part at the middle section of the valve, the part used to position the flange of the middle section of the valve becomes unnecessary, enabling a reduction in the diameter of the center section of the needle-less connector.

The basic shape of the protruding support surface 32 is also not limited to the structures as shown. For example, the crest section side 36 of the flexion section side 42 may have a tapered surface shape having a nearly constant tilt angle as with the foot section side 34 without the provision of a recessed curved surface 40. In this case, a flexion section can be provided by setting a smaller tilt angle on the apex 38 side in comparison to the tilt angle on the foot section side 34. Furthermore, the flexion section does not have to be outwardly convexed. For example, by providing a recessed curved surface on a sloped surface having to constant tilt angle, a flexion section can also be formed at the edge of the recessed curved surface.

The crest section side 36 of the protruding support surface 32 may have a center axis rotational symmetry shape instead of a mountain-shape as illustrated. For example, the center axis rotational symmetry-shaped protruding support surface of FIG. 1 can be used provided that the protruding support surface has a sloped surface which slopes so that the center section protrudes.

As mentioned above, when the protruding support surface 32 is given a center axis rotational symmetry shape or a tapered surface shape having a nearly constant tilt angle, the inner surface of the recess 64 on the lower valve 14 is also formed to have a corresponding shape, which is superposed onto the protruding support surface 32 so as to be in close contact therewith.

In the above embodiment, the flexion section 42 is provided near the center section of the protruding support surface 32 in the direction of height. However, this is not limited to the above. For example, flexion sections may be provided at sections biased to the upper side or lower side in the direction of height of the protruding support surface 32 to vary the tilt angle of the protruding support surface 32. In this case, the upper end edge of the recessed curved surface 40 of the above embodiment may also be treated as a flexion section. In this manner, there may be a plurality of flexion sections on the protruding support surface 32 in the direction of height.

In the case of a plurality of flexion sections as mentioned above, the protruding support surface 32 may also have a stepped or waved shape or a combination of the above. In other words, the protruding support surface 32 is not limited to any shape provided that the above-mentioned action and effect is carried out, and may, for example, have a left-right asymmetric front or side view.

In the above embodiment, the recessed curved surface 40 is formed in the nearly middle section of the protruding support surface 32 in the direction of height, and the lower end edge of the recessed curved surface 40 constitutes the flexion section 42. However, this is not limited to the above. In other words, the position of the recessed curved surface 40 may also be biased on the upper side or the lower side in the direction of height of the protruding support surface 32. Furthermore, in the above embodiment, the recessed curved surface 40 is bored into the sloped surfaces on both sides of the protruding support surface 32. However, this may take the form of a ring shape around the entire circumference or there may be a plurality of ring shapes. In other words, the position, shape or number of recessed curved surfaces 40 is unrestricted provided that the above-mentioned action and effect is carried out.

For example, the lower side of the recessed curved surface 40, or in other words, the foot section side 34 of the protruding support surface 32 in the above embodiment is not necessary, where the flat surface 44 and the lower end edge of the recessed curved surface 40 may be in contact.

As mentioned above, there are many shapes for the protruding support surface 32 or the recessed curved surface 40. In any case, the shape of the inner surface of the recess 64 of the lower valve 14 must have a corresponding shape.

KEYS TO SYMBOLS

10, 100, 104: Needle-less connector, 12: Housing, 14, 101: Lower valve (Elastic valve body), 16: Upper valve (Secondary valve body), 28: Drug solution flow path, 32: Protruding support surface, 34: Foot section side, 36: Crest section side, 38: Apex, 40: Recessed curved surface, 41: Tip end opening, 42: Flexion section, 56: Valve body part, 62, 75: Slit, 63: Flange part, 78: Deformation allowance space, 92: Male luer

The invention claimed is:

1. A needle-less connector comprising:
   a housing including a peripheral wall part and a cylindrical part, the peripheral wall part being provided away from an outer circumferential side of the cylindrical part, an inner peripheral surface of the cylindrical part of the housing forming a drug solution flow path, the drug solution flow path having a tip end opening that is formed by a tip end of the cylindrical part; and
   an elastic valve body that is provided at a tip end opening of the drug solution flow path, the elastic valve body being formed with a first slit that penetrates through the elastic valve body, such that insertion of a male luer into the first slit opens the elastic valve body and connects the male luer to the drug solution flow path,
   wherein the cylindrical part of the housing includes a protruding support surface whose center section protrudes and slopes in a direction of a foot, the protruding support surface being formed by an outer peripheral surface of the tip end of the cylindrical part, arranged in an inner area that is surrounded by the peripheral wall part of the housing, and formed separately from the elastic valve body,
   the elastic valve body is superposed onto the protruding support surface in a state of close contact with the protruding support surface,
   the insertion of the male luer into the slit of the elastic valve body causes expanding deformation of the elastic valve body in an outward direction away from the protruding support surface,
   a flexion section is formed on a sloped surface of the protruding support surface, the sloped surface having different tilt angles on a foot section side and on a crest section side of the flexion section, and
   the sloped surface on the crest section side of the flexion section in the protruding support surface constitutes a recessed curved surface.

2. The needle-less connector according to claim 1, wherein a deformation allowance space is provided on an outer peripheral side of the elastic valve body.

3. The needle-less connector according to claim 1, wherein
   the elastic valve body integrally includes (i) a valve body part in which the first slit is formed penetrating through the valve body part, and (ii) a pair of flange parts arranged at both ends of the first slit of the valve body part in a direction of penetration, each of the pair of flange parts extending to an outer peripheral side, and
   an outer peripheral edge part of each of the pair of flange part is fixed to and supported by the housing, and elastic deformation of the elastic valve body is allowed between opposing faces of the flange parts.

4. The needle-less connector according to claim 1, wherein a space communication passage is formed to enable communication between an outer space and an area that is provided on an outer peripheral side of the elastic valve body and that allows an elastic deformation of the elastic valve body.

5. The needle-less connector according to claim 1, wherein
   an elastic secondary valve body is provided so as to be superposed onto an outer end surface of the elastic valve body, and
   a second slit is provided on the elastic secondary valve body for insertion of the male luer, the second slit extending in a direction to intersect the first slit of the elastic valve body and be superposed onto the elastic valve body.

6. The needle-less connector according to claim 1, wherein
   at least a tip end section of the protruding support surface extends in a mountain-like shape by means of a ridge-shaped apex,
   the flexion section is formed on the sloped surface on each side of the ridge-shaped apex, and
   the first slit of the elastic valve body is superposed so as to extend along the ridge-shaped apex of the protruding support surface.

7. The needle-less connector according to claim 1, wherein the foot section side of the flexion section in the protruding support surface has a tapered surface.

8. The needle-less connector according to claim 1, wherein the tip end opening of the drug solution flow path has a nozzle shape whose cross-sectional area is reduced.

9. The needle-less connector according to claim 1, wherein the elastic valve body integrally includes (i) a valve body part in which the first slit is formed, the first slit penetrating through the valve body part, and (ii) a flange part arranged at an upper end of the valve body part, the flange part extending to an outer peripheral side of the valve body part, wherein an outer peripheral section of the flange part is fixed to and supported by the housing.

10. The needle-less connector according to claim 9, further comprising a holding sleeve disposed about the valve body part, wherein the outer peripheral section of the flange part is pressed between an upper end face of the holding sleeve and the housing so that the outer peripheral section of the flange part is fixed to the housing to seal the valve body part and the housing.

11. The needle-less connector according to claim 1, wherein a bending section is formed on the elastic valve body, the bending section being superposed onto the protruding support surface in a state of close contact with the protruding support surface, and at a position corresponding to the flexion section of the protruding support surface.

* * * * *